United States Patent [19]
Dobbs et al.

[11] Patent Number: 6,094,469
[45] Date of Patent: Jul. 25, 2000

[54] COMPUTED TOMOGRAPHY SYSTEM WITH STABLE BEAM POSITION

[75] Inventors: John Dobbs, Hamilton; Ruvin Deych, Burlington; James Bowers, Danvers, all of Mass.

[73] Assignee: Analogic Corporation, Centennial Industrial Park, Mass.

[21] Appl. No.: 09/176,444

[22] Filed: Oct. 21, 1998

[51] Int. Cl.⁷ ........................................................ A61B 6/00
[52] U.S. Cl. .............................. 378/19; 378/207; 378/901
[58] Field of Search .......................... 378/4–19, 137–138, 378/121, 113–114, 116, 145–161, 207, 901

[56] References Cited

U.S. PATENT DOCUMENTS

| | | |
|---|---|---|
| 4,559,639 | 12/1985 | Glover et al. . |
| 4,769,827 | 9/1988 | Uno et al. . |
| 4,803,711 | 2/1989 | Tsujii et al. . |
| 4,991,189 | 2/1991 | Boomgaarden et al. . |
| 5,065,420 | 11/1991 | Levene . |
| 5,131,021 | 7/1992 | Gard et al. . |
| 5,299,250 | 3/1994 | Styrnol et al. . |
| 5,469,429 | 11/1995 | Yamazaki et al. . |
| 5,550,886 | 8/1996 | Dobbs et al. . |
| 5,550,889 | 8/1996 | Gard et al. . |
| 5,579,359 | 11/1996 | Toth . |
| 5,706,326 | 1/1998 | Gard et al. . |
| 5,745,548 | 4/1998 | Dobbs et al. . |

*Primary Examiner*—K. P. Hantis
*Attorney, Agent, or Firm*—McDermott, Will & Emery

[57] ABSTRACT

A computed tomography system having a fourfold improvement in both short-and long-term beam position stability. A beam-position detector is located at a peripheral edge of the primary fan beam and is fixed relative to the primary detectors so as to indicate beam position on the primary detectors. The beam-position detector is oriented so that its maximum sensitivity to beam motion is in the direction of beam movement due to focal spot drift due to thermal effects and gravity. Short-term focal spot drift is detected by a secondary beam out of the primary fan beam and is corrected in real time by adjusting the position of a collimator for the primary beam. Long-term changes in the focal spot position are corrected by using information from the beam-position detector to recalibrate the focal spot-beam collimator data set.

22 Claims, 2 Drawing Sheets

COMPUTED TOMOGRAPHY SYSTEM WITH STABLE BEAM POSITION

TECHNICAL FIELD

The invention relates generally to computed tomography scanning systems in which both an x-ray source and an array of x-ray detectors rotate about an object to be scanned, and more particularly to subsystems in such scanners for maintaining a desired average position of a collimated x-ray beam on the detectors.

BACKGROUND OF THE INVENTION

Computed tomography systems typically include a radiation source which transmits an electron beam towards and onto an anode to define a focal spot from which the radiation is emitted. One or more beam collimators defines a fan-shaped beam emanating from the focal spot, and a bank of x-ray detectors located opposite the radiation source receives the x-ray beam. In third-generation computed tomography systems, the radiation source and the x-ray detectors are both mounted on a rotatable gantry for rotation around an object to be scanned.

The anode is subject to overheating from impingement of the electron beam on it. It is thus designed to rotate rapidly so that the electron beam does not strike the anode in any single location for more than a fraction of a second, thereby reducing the risk of localized overheating and possible melting of a portion of the anode.

Notwithstanding the rotation of the anode, heat from the electron beam causes the anode and its support structure to expand, and this causes the focal spot on the anode to drift. The effects of gravity and rotation of the radiation source also contribute to focal spot drift. Such focal spot drift typically occurs in the axial, or z, direction and causes the fan beam to change its position on the primary x-ray detectors, also in the z direction. Changes in beam position on the primary detectors may produce variations in the gain and energy sensitivity of the detectors, particularly if the detectors are calibrated and then not used until some time (days or weeks) later. This can cause ring artifacts to appear in the reconstructed image.

It is known to correct or compensate for focal spot drift by, for example, using x-ray detectors which are highly uniform in the z direction, and thus insensitive to beam motion in the z direction. However, solid-state detectors having this characteristic are very expensive to manufacture. Gas detectors are a less expensive alternative. Although xenon gas detectors are more uniformly sensitive than solid-state detectors, they are significantly less efficient and are therefore not a desirable alternative.

Another method of correcting focal spot drift is to use a post-patient collimator positioned between the object being scanned and the detectors. The post-patient collimator is preferably located as close to the detectors as is practical and restricts the size of the beam so that the beam that reaches the detectors is smaller than the beam that reaches the patient. As the beam moves in the z direction, the edges of the beam are masked by the post-patient collimator and never impinge on the detectors. The collimated beam impinging on the detectors can therefore be maintained in a fixed position relative to the detectors.

A disadvantage of this technique is that a potentially significant amount of radiation may pass through the patient without being detected. The patient is thus exposed to radiation in excess of that which is used to provide diagnostic information.

In the prior art, the beam position on the x-ray detectors may be sensed by a reference detector located, for example, at a peripheral edge of the beam. The portion of the beam directed to a peripherally-located reference detector is usually not occluded or shadowed by any object in its path. Thus, the magnitude of the signals from the reference detector should always be a constant value, except when the reference detector is obstructed or occluded. This approach is disclosed in, for example, U.S. Pat. Nos. 4,559,639 to Glover et al., 5,550,889 to Gard et al., 5,706,326 to Gard, 5,299,250 to Stymol et al., 5,131,021 to Gard et al., 5,065,420 to Levene, 4,991,189 to Boomgaarden et al., and 4,769,827 to Uno et al.

A disadvantage to the use of one or more reference detectors at a peripheral edge of the fan beam is that they are occasionally occluded, or shadowed, by the patient. If this happens, the reference detector will provide signals of varying, not constant, magnitude, which could indicate either that the beam has changed its position on the primary detectors, or the variation in signal magnitude is caused by shadowing of the reference detector. The reference detector will thus be unreliable for providing a signal of constant magnitude and thus cannot be used to confirm a constant beam position on the primary detector array.

To avoid the problem of a shadowed peripherally located reference detector, the reference detector can instead be located so that the portion of the x-ray beam reaching the reference detector is never occluded, such as, for example, between a beam-defining precollimator and the x-ray tube. In this approach, a separate, secondary beam is directed from the focal spot towards a secondary detector which may be out of the plane of, or beyond the edges of, the primary beam. Movement of the secondary beam relative to the reference detector indicates drift of the focal spot. A desired beam position on the primary detectors can be monitored and maintained in response to a signal from the reference detector, which drives a beam-defining collimator to place the beam in a desired position. This technique is disclosed in, for example, U.S. Pat. No. 5,550,886 to Dobbs et al., hereby incorporated by reference, as well as U.S. Pat. Nos. 5,469,429 to Yamazaki et al. and 4,803,711 to Tsujii et al.

The reference detector must be calibrated to achieve a desired primary beam position as a function of focal spot position. The long-term stability of the reference detector is a function of the stability of its calibration.

The prior art addresses the problem of long-term thermal drift of the focal spot and other system components, but not the problem of gravity-induced focal spot drift, which is a sinusoidal variation which occurs over the course of a single rotation of the system components.

Thus, there is a need for a computed tomography scanner which can provide a stable beam position on the primary detectors over both the long and short term, i.e., during many rotations of the source and detectors in a period which may span days, weeks, months or even longer, as well as during a single rotation of the source and detectors.

SUMMARY OF THE INVENTION

The present invention provides both short-term and long-term beam position stability by compensating for focal spot drift caused by both short-and long-term influences. According to one aspect of the invention, there is provided a computed tomography system including a radiation source, a primary array of x-ray detectors adapted to receive a beam of x-radiation produced at a focal spot of the source, and a fan beam collimator positionable between the focal spot and the primary detector array for defining the fan beam. The radiation source and the primary detector array are supported on a rotatable gantry for rotation about an object to be scanned. The tomography system maintains an alignment between the fan beam and the detectors of the primary array during a rotation of the source and detectors and continuously recalibrates the beam collimator and focal spot position throughout an integer number of rotations of the source and detectors so as to maintain a desired position of the fan beam on the detectors of the primary array. The system comprises:

means for detecting a change in the position of the focal spot and for moving the fan beam collimator in response to the change in focal spot position so as to maintain a desired beam position on the detectors of the primary detector array;

means for correlating the position of the fan beam collimator with the position of the focal spot and for establishing a corresponding set of calibration data;

means for defining a desired average position of the fan beam on the detectors of the primary array, and for detecting, throughout an integer number of rotations of the system, a deviation of an actual average fan beam position on the detectors of the primary array during a given rotation of the system from the desired average fan beam position on the detectors of the primary array; and means for correcting the calibration data so as to maintain the desired average position of the fan beam on the detectors of the primary array.

The means for detecting a change in the position of the focal spot and for moving the fan beam collimator in response to that change preferably includes means for defining a secondary beam of radiation produced at the focal spot and directed out of the fan beam, such as out of the plane of the fan beam or beyond the edges of the fan beam. A secondary beam detector responsive to the secondary beam of radiation detects a change in the position of the focal spot in the z-axis direction and generates a control signal for controlling movement of the fan beam collimator.

The means for detecting a deviation of an actual average fan beam position from the desired average fan beam position preferably comprises a beam-position detector proximal to the primary detector array and substantially within the fan beam. The beam-position detector is preferably located at a peripheral edge of the fan beam.

In a preferred embodiment, the beam-position detector is preferably oriented so that its greatest sensitivity to changes in beam position is in the z direction. Accordingly, the principal axis of the beam-position detector is preferably substantially transverse to the principal axes of the detectors of the primary array. In an especially preferred embodiment, the principal axis of the beam-position detector makes an angle of approximately 82° with the principal axes of the detectors of the primary array.

The means for correcting the calibration data preferably includes means for determining the presence and absence of a detectable object within the portion of the fan beam that impinges on the beam-position detector. Only information generated by the beam-position detector in the absence of a detectable object within that portion of the fan beam is used to correct the calibration data. Signals from the beam-position detector at any time are compared to signals from the beam-position detector at a time when it is known not to be shadowed by any object in the beam.

Because the variation in the position of the beam on the primary detectors is a sinusoidal function of the gravitational force on the x-ray source and detectors, the desired position of the beam on the detectors of the primary array is an average beam position which is determined over an integer number of rotations of the source and the detectors, and not over a partial rotation or rotations.

These and other objects and advantages of the invention will in part be obvious and will in part appear hereinafter. The invention accordingly comprises the apparatus possessing the construction, combination of elements and arrangement of parts which are exemplified in the following detailed disclosure, the scope of which will be indicated in the claims.

BRIEF DESCRIPTION OF THE DRAWINGS

For a fuller understanding of the nature and objects of the present invention, reference should be made to the following detailed description taken in connection with the accompanying drawings, in which.

DETAILED DESCRIPTION OF THE DRAWINGS

Figure 1:
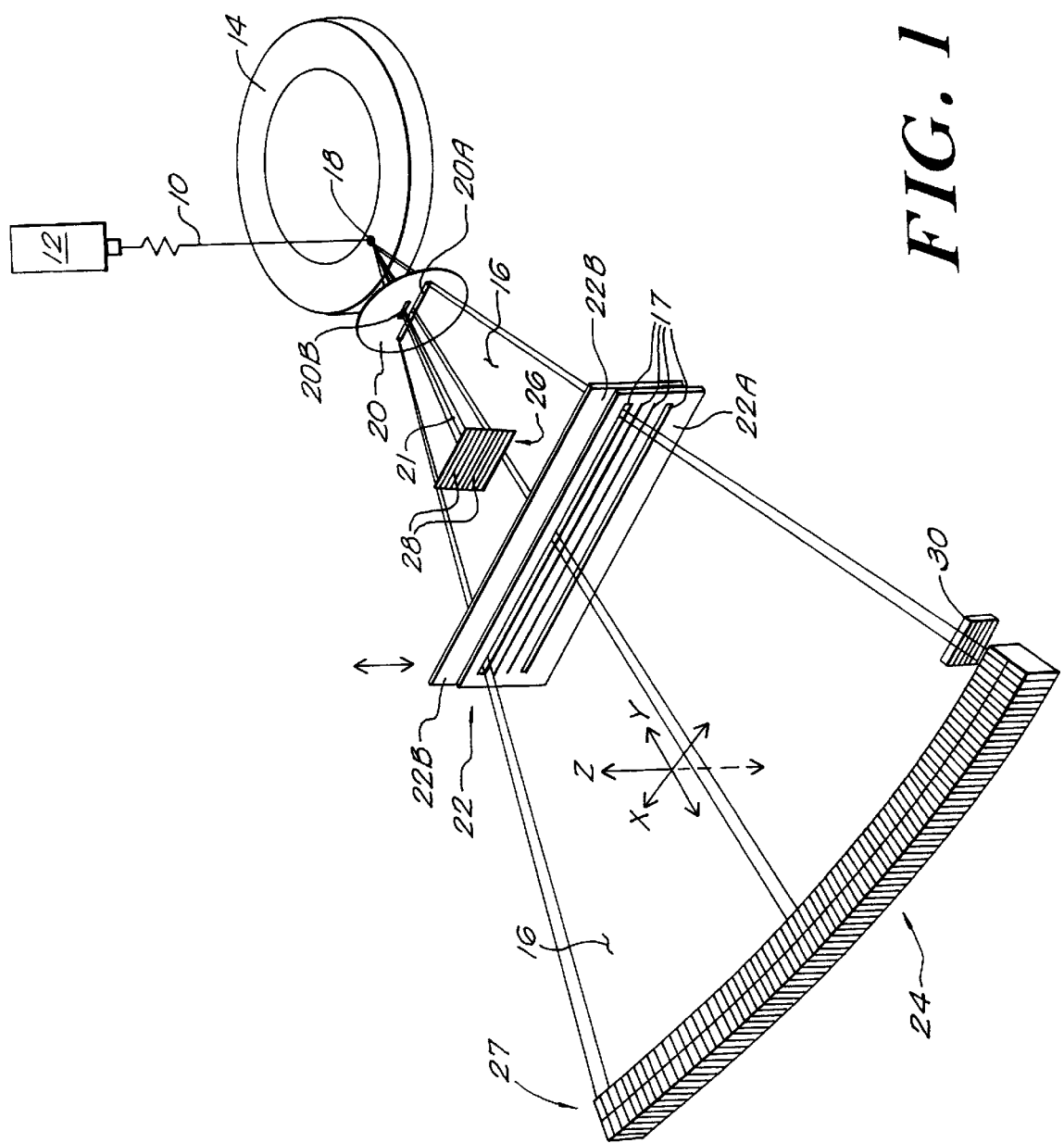
FIG. 1 is a simplified perspective view of the fan beam-defining components or subsystem of the computed tomography scanner of the present invention.
Figure 2:
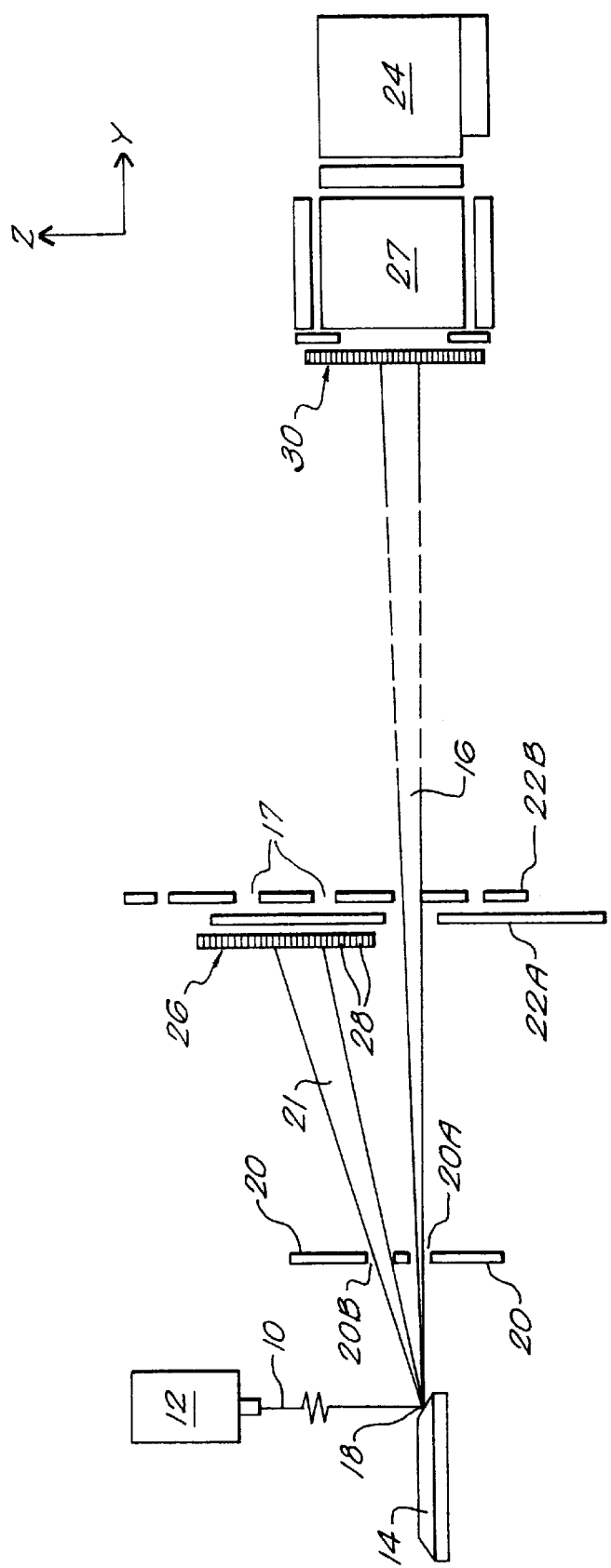
FIG. 2 is a simplified side view of the components of the subsystem of FIG. 1.

The components of a fan beam-defining subsystem of a tomography system according to the present invention are shown in perspective in FIG. 1 and in side view in FIG. 2. The respective axes x, y and z are shown in each FIGURE also. An electron beam 10 is directed from a source 12 of electrons toward an anode 14. The point on the anode from which a fan-shaped x-ray beam 16 emanates defines the focal spot 18 of the system. The x-ray beam 16 is collimated through a series of collimators 20, 22 and is received by an array of x-ray detectors 24. A corresponding array of anti-scatter plates 27 may be arranged in front of the detectors, as shown in FIG. 2. An object to be scanned, such as a human patient (not shown), is disposed within the fan beam between the beam collimators and the detectors. In a third-generation computed tomography system, including that of the present invention, the x-ray source and detectors rotate around a common isocenter, and the patient remains stationary.

A precollimator 20 includes a principal slit 20A which restricts the extent of the fan beam of X-rays emanating from the focal spot of the source in the x and z directions. The principal slit 20A is disposed relatively close to the source. The precollimator 20 is made of a material impervious to X-rays, such as lead, tungsten or tantalum and alloys thereof. The precollimator 20 is fixed with respect to the focal spot and detectors and does not move. As detailed more fully below, the precollimator may include a secondary slit 20B which defines radiation beam 21 which is directed out of the primary beam, either by directing it out of the plane of the primary beam, as shown most clearly in FIG. 2, or by directing it beyond the edges of the primary fan beam.

A slice-defining collimator 22 defines the thickness (z dimension) and arcuate extent (x dimension) of the fan beam 16. As shown in FIG. 1, the slice-defining collimator 22 comprises a first plate 22A having a plurality of slits 17 of different heights, and a second solid plate 22B. The plates can be moved relative to each other so as to permit the beam 16 to pass through a single slit of a desired height and length. The height of the slit defines the thickness (z dimension) of the beam passing through the object being scanned and coincident on the array of primary detectors, while the length of the slit defines the arcuate extent (x dimension) of the beam. Preferably, the slit is dimensioned so that the beam is substantially centered on the detectors in the z dimension and extends only a small amount beyond the peripheral detectors of the array.

In the prior art tomography systems the anode 14 and its support structure expands due to heat generated by the source as it produces the electron beam, and contracts when the source stops producing the electron beam and the heat on the anode is dissipated. Such thermal expansion and contraction causes the focal spot 18 to shift in the z direction. The shift of the focal spot in the z direction changes the angle at which the beam 16 passes through the collimators 20, 22 and thus changes the position of the beam 16 on the primary detectors 24. Beam motion on the detectors may cause a change in the gain and/or the energy sensitivity of the detectors, which may be manifested as ring artifacts in the reconstructed image.

To compensate for shifts of the focal spot 18 in the z direction, a secondary slit 20B is provided in the precollimator 20 for defining and directing a secondary beam 21, in this illustration, out of the primary fan beam onto a secondary monitoring device 26. As illustrated most clearly in FIG. 2, this slit 20B provides for a beam directed out of the primary fan beam. As previously mentioned, the secondary slit 20B could be positioned to provide a secondary beam 21 that lies substantially within the primary fan beam plane but beyond the edges of the primary fan beam. The secondary monitoring device preferably includes a plurality of X-ray detectors 28 arranged in a stacked linear array for providing an output signal as a function of the position of the secondary beam on the secondary detector array.

The secondary detectors 28 and the secondary beam 21 measure the position of the focal spot 18 and provide information for controlling the position of the primary beam 16 on the primary detectors 24 in real time. Information about the position of the focal spot, as well as calibration information relating the focal spot position to the position of the slice-defining collimator 22, provides the necessary information for controlling and maintaining a correct position for the beam 16 on the detectors of the primary array. However, the calibration itself is subject to long-term drift as a result of heating and cooling of the tomography system components.

According to the present invention, the tomography system includes a beam-position detector 30 at a peripheral edge of the primary detector array for directly measuring the position of the primary fan beam 16 on the primary detectors 24 over an integer number of rotations of the source and detectors. The beam-position detector 30 can be used to recalibrate the focal spot and slice-defining collimator positions. During the relatively long period of time in which the focal spot 18 drifts and the slice-defining collimator 22 is repositioned, thereby calibrating the focal spot position to the slice-defining collimator position, there will be many opportunities to obtain data from a complete 360° rotation of the primary detector array, and thus from the beam-position detector 30, when the portion of the beam 16 impinging on it is not occluded by any object. This data is used to adjust the zero point of the calibration data.

The beam-position detector 30 is preferably disposed at a peripheral edge of the fan beam 16 and is spatially fixed relative to the primary detectors so that movement of the primary beam 16 relative to the primary detectors 24 is also relative to the beam-position detector 30. As shown most clearly in FIG. 2, the beam-position detector 30 is preferably oriented so that its maximum sensitivity to changes in the position of the beam is in the z direction. In particular, it is oriented to be substantially transverse, and preferably approximately perpendicular, to the principal axes of motion sensitivity of the primary detectors. In a preferred embodiment, the principal axis of the beam-position detector 30 makes an angle of about 82° with the principal axes of the primary detectors. In contrast, the primary detectors 24 are generally oriented so that their maximum sensitivity to beam position is in the x direction. They are thus relatively insensitive to beam movement in the z direction. Accordingly, they cannot be reliable indicators of movement of the beam in the z direction.

In a preferred embodiment, the beam-position detector 30 is, for example, a photodiode. Typically a photodiode used for this purpose absorbs only about 15% of the beam, and thus it can conveniently be placed so that it is in front of, and thus overlaps, one or more of the primary detectors in the main detector array. Thus, it does not occupy or require any additional circumferential space beyond the arcuate extent of the primary detectors 24. The photodiode also does not significantly attenuate the radiation beam and thus does not significantly diminish the diagnostic information contained within the beam.

The beam-position detector 30 can include, for example, a comparator function for determining whether a detectable object is present within the primary fan beam and is casting a shadow on some or all of the detectors 24. The comparator evaluates and compares normalized signals from the beam-position detector at any time to normalized signals from the beam-position detector at a time when it was known to be unshadowed. If an object is casting a shadow on the beam-position detector at any time within a complete rotation of the source and detectors, the information from the beam-position detector is not used for recalibrating the zero point of the calibration data set for the respective focal spot and slice-defining collimator positions.

During gain calibration of the primary detectors 24, the beam-position detector 30 and the secondary beam detector 28 provide signals representative of no patient or other obstruction in the beam. The object of calibration of the system without a patient in the beam is to ensure that the primary beam always impinges on the same portion of a given detector, so as to ensure that the magnitude of the signal from that detector is substantially constant.

As the patient is scanned, raw information is obtained and stored. After a patient scan, the data acquisition system (DAS) computer can determine if there is a set of data corresponding to a full 360° rotation of the source and detectors with no shadowing of the beam-position detector. If such a data set is available, it can be used to calibrate the focal spot position with the slice-defining collimator position and correct any deviation of the actual beam position from the desired beam position. The desired beam position is actually an average of the desired beam positions over one or more integer number of (i.e., complete 360°) rotations of the source and detectors. The calibration of the focal spot position with the slice-defining collimator position can be continuously recalibrated as long as the beam-position detector is not obstructed over a full rotation of the system.

The beam position on the detectors of the primary array is expressed using the first moment, or centroid, as described more fully in U.S. Pat. No. 5,550,886 to Dobbs et al. The beam position as determined by the beam-position detector is checked for obstruction. If no obstruction is present, the data are averaged over a full 360° rotation of the source and detectors. When a full rotation of views in sequence are processed a new correction value is computed. If less than a full rotation of views is available (e.g., if the patient obstructs some of the views within a single rotation), no correction value is computed. When a full rotation of views have been accumulated, the centroid is computed and used to correct the next adjustment of the slice defining collimator. This process continues as long as the scanner is operating, i.e., as long as the x-ray source is providing x-rays.

Because the secondary detector 26 indicates short-term (i.e., within a single rotation of the source and detectors) motion of the focal spot 18 which causes changes in the fan beam position on the primary detectors within a single rotation, the beam position can be stabilized within a single rotation. Long-term drift of the focal spot can also be sensed and corrected. Long-term drift of the system geometry causing calibration errors can be detected and corrected by the beam-position detector 30 whenever data from a full rotation, which are not corrupted by the presence of a patient in the beam, are obtained.

With the calibration subsystem of the present invention, the beam position over an integer number of rotations of the source and detectors is stable to within 100 micrometers. Previously, long-term stability of the average beam position was within approximately 400 micrometers. Stability of the beam position is thus improved by a factor of at least 4 over the prior art systems. This improvement in beam position stability improves the quality of the reconstructed image and enables the scanner to be built less expensively.

Because certain changes may be made in the above apparatus without departing from the scope of the invention herein disclosed, it is intended that all matter contained in the above description or shown in the accompanying drawings shall be interpreted in an illustrative and not a limiting sense.

We claim:

1. In a computed tomography system including a radiation source, a primary array of x-ray detectors adapted to receive a beam of x-radiation produced at a focal spot of the source, wherein the radiation source and the primary detector array are supported on a rotatable gantry for rotation about an object to be scanned, and a fan beam collimator positionable between the focal spot and the primary detector array for defining the fan beam, means for maintaining an alignment between the fan beam and the detectors of the primary array during a rotation of the source and detectors and for continuously calibrating the system to maintain a desired position of the fan beam on the detectors of the primary array throughout an integer number of rotations of the system, comprising:

means for detecting a change in the position of the focal spot and for moving the fan beam collimator in response to said change so as to maintain a desired beam position on the detectors of the primary detector array;

means for correlating the position of the fan beam collimator with the position of the focal spot to establish a corresponding set of calibration data;

means for defining a desired average position of the fan beam on the detectors of the primary array, and for detecting, for an integer number of rotations of the system, a deviation of an actual average fan beam position on the detectors of the primary array from the desired average fan beam position on the detectors of the primary array; and means for correcting the calibration data so as to maintain the desired average position of the fan beam on the detectors of the primary array.

2. A system according to claim 1, wherein said means for detecting a change in the position of the focal spot and for moving the fan beam collimator includes:

means for defining a secondary beam of radiation produced at the focal spot and directed out of the fan beam; and secondary beam detecting means responsive to the secondary beam of radiation for detecting a change in the position of the focal spot in the z-axis direction and for generating a control signal representative of the change in position of the focal spot for controlling movement of the fan beam collimator.

3. A system according to claim 2, wherein the secondary beam is directed out of the plane of the primary fan beam.

4. A system according to claim 2, wherein the secondary beam is disposed substantially within the plane of the primary fan beam and beyond the edges of the primary fan beam.

5. A system according to claim 2, wherein the means for detecting a deviation of an actual average fan beam position from the desired average fan beam position comprises a beam-position detector disposed proximal to the primary detector array and substantially within the fan beam.

6. A system according to claim 5, wherein said beam-position detector is disposed at a peripheral edge of the fan beam.

7. A system according to claim 6, wherein the beam-position detector is oriented so that its greatest sensitivity to changes in the position of the fan beam is in the direction of the z-axis.

8. A system according to claim 7, wherein the principal axis of the beam-position detector is substantially transverse to the principal axes of the detectors of the primary array.

9. A system according to claim 8, wherein the principal axis of the beam-position detector makes an angle of approximately 82° with the principal axes of the detectors of the primary array.

10. A system according to claim 8, wherein said means for correcting the calibration data includes means for determining the presence and absence of a detectable object within the portion of the fan beam that impinges on the beam-position detector and for using only information generated by the beam-position detector in the absence of a detectable object within that portion of the fan beam to correct the calibration data.

11. A system according to claim 10, wherein said means for determining the presence and absence of a detectable object within the fan beam includes means for comparing signals from the beam-position detector at any time to signals from the beam-position detector at a time at which it is known not to be shadowed by an object in the portion of the fan beam that impinges on the beam-position detector.

12. A system according to claim 11, wherein the desired position of the beam on the detectors of the primary array is an average position of the beam on the detectors which is determined over an integer number of rotations of the source and detectors.

13. In a computed tomography system including a radiation source, a primary array of x-ray detectors adapted to receive a beam of x-radiation produced at a focal spot of the source, a rotatable gantry for supporting the radiation source and the primary detector array for rotation about an object to be scanned, a fan beam collimator positionable between the focal spot and the primary detector array for defining the fan beam, means for detecting a change in the position of the focal spot and for moving the fan beam collimator in response to the change so as to maintain an alignment between the fan beam and the detectors of the primary detector array, and means for correlating the position of the fan beam collimator with the position of the focal spot and for establishing a corresponding set of calibration data, a continuous calibration system for maintaining a desired average position of the fan beam on the detectors of the primary array, comprising:

means for defining a desired average position of the fan beam on the detectors of the primary array, and for detecting, throughout an integer number of rotations of the system, a deviation of an actual average fan beam position on the detectors of the primary array from the desired fan beam position on the detectors of the primary array; and means for correcting the calibration data so as to maintain the desired average position of the fan beam on the detectors of the primary array.

14. A continuously self-calibrating computed tomography system, comprising:

a radiation source for generating x-rays from a focal spot;

a primary array of x-ray detectors for receiving radiation from the source during a tomographic scan;

means for rotating the source and x-ray detectors about a Z-axis during a tomographic scan;

a fan beam collimator positioned relative to the focal spot for collimating radiation emanating from the focal spot so as to define a primary fan beam of radiation emanating from the focal spot onto the detectors of the primary array during a tomographic scan;

means for defining a secondary beam of radiation emanating from the focal spot and out of the fan beam;

secondary beam detecting means, responsive to the secondary beam of radiation, for sensing a change in the position of the focal spot and for generating a position signal representative of the change in position of said focal spot;

means, responsive to the position signal, for moving the fan beam collimator so as to maintain an alignment of the primary fan beam of radiation and the detectors of the primary array;

means for correlating the position of the fan beam collimator with the position of the focal spot and for establishing a corresponding set of calibration data;

means for defining a desired average position of the fan beam on the detectors of the primary array, and for detecting, throughout an integer number of rotations of the system, a deviation of an actual average fan beam position on the detectors of the primary array from the desired average fan beam position on the detectors of the primary array; and means for correcting the calibration data so as to maintain the desired average position of the fan beam on the detectors of the primary array.

15. A system according to claim 14, wherein the means for detecting a deviation of an actual average fan beam position from the desired average fan beam position comprises a beam-position detector disposed proximal to the primary detector array and substantially within the fan beam.

16. A system according to claim 15, wherein the beam-position detector is disposed at a peripheral edge of the fan beam.

17. A system according to claim 16, wherein the beam-position detector is oriented so that its greatest sensitivity to changes in the position of the fan beam is in the direction of the z-axis.

18. A system according to claim 17, wherein the principal axis of the beam-position detector is substantially transverse to the principal axes of the detectors of the primary array.

19. A system according to claim 18, wherein the principal axis of the beam-position detector makes an angle of approximately 82° with the principal axes of the detectors of the primary array.

20. A system according to claim 18, wherein said means for correcting the calibration data includes means for determining the presence and absence of a detectable object within the portion of the fan beam that impinges on the beam-position detector and for using only information generated in the absence of a detectable object within that portion of the fan beam to correct the calibration data.

21. A system according to claim 20, wherein said means for determining the presence and absence of a detectable object within the fan beam includes means for comparing signals from the beam-position detector at any time to signals from the beam-position detector at a time at which it was known not to be shadowed by an object in the portion of the fan beam impinging on the beam-position detector.

22. A system according to claim 21, wherein the desired position of the beam on the detectors of the primary array is an average beam position which is determined over an integer number of rotations of the source and detectors.

* * * * *